(12) United States Patent
Chang et al.

(10) Patent No.: US 12,052,812 B2
(45) Date of Patent: Jul. 30, 2024

(54) CAPACITOR CAPABLE OF RELEASING REACTIVE OXYGEN SPECIES AND REACTIVE NITROGEN SPECIES AFTER POWERING

(71) Applicants: Chung-Tai Chang, Tainan (TW); Chia-Hao Chang, Tainan (TW); Ting-Yi Chang, Tainan (TW)

(72) Inventors: Chung-Tai Chang, Tainan (TW); Chia-Hao Chang, Tainan (TW); Ting-Yi Chang, Tainan (TW)

(*) Notice: Subject to any disclaimer, the term of this patent is extended or adjusted under 35 U.S.C. 154(b) by 157 days.

(21) Appl. No.: 17/893,366

(22) Filed: Aug. 23, 2022

(65) Prior Publication Data

US 2024/0074027 A1 Feb. 29, 2024

(51) Int. Cl.
*H01H 1/24* (2006.01)
*H01H 1/46* (2006.01)
*H05H 1/46* (2006.01)

(52) U.S. Cl.
CPC .......... *H05H 1/46* (2013.01); *H05H 2245/30* (2021.05)

(58) Field of Classification Search
CPC .......... H05H 1/24; H05H 1/2439; H05H 1/46; H05H 1/466; H05H 1/2406; H05H 2245/00; H05H 2245/30; H05H 2245/34
See application file for complete search history.

(56) References Cited

U.S. PATENT DOCUMENTS

| | | | |
|---|---|---|---|
| 2017/0112157 A1* | 4/2017 | Keener | A61L 2/14 |
| 2017/0183631 A1* | 6/2017 | Keidar | H05H 1/245 |
| 2020/0305265 A1* | 9/2020 | Eckert | A61B 18/042 |
| 2021/0308309 A1* | 10/2021 | Hochwalt | A61L 2/0094 |

FOREIGN PATENT DOCUMENTS

WO WO-2022248097 A1 * 12/2022 ............ A01P 1/00

OTHER PUBLICATIONS

Decision on Granting—RU Application No. 2022122728/07(048488)—Dated Feb. 9, 2024—14 pages (Original RU Notice and English translation of same.).

(Continued)

*Primary Examiner* — Thai Pham
(74) *Attorney, Agent, or Firm* — Best & Flanagan LLP

(57) ABSTRACT

A capacitor capable of releasing reactive oxygen species and reactive nitrogen species after powering of claim 1 is composed of the dielectric material. A plurality of through holes are designed on the capacitor, the through holes being used as air gaps to supply plasma gas and blow a fan to increase the gas flow, and the voltage being connected to the two corresponding electrode edges of the capacitor so that the capacitor generating a heating temperature (lower than 200 degrees Celsius). Thereby, after the capacitor is perforated to form honeycomb shape and powered, the air surrounding the capacitor flowing through the capacitor is ionized to the oxygen ion and nitrogen ion via heating and charge-discharge, generates plasma at room temperature and atmospheric pressure and releases the reactive oxygen ions and reactive nitrogen ions healing and helpful for body healing.

6 Claims, 4 Drawing Sheets

(56) References Cited

OTHER PUBLICATIONS

Nazir Barekzi and Mounir Laroussi, Effects of Low Temperature Plasmas on Cancer Cells, Plasma Processes and Polymers, Oct. 29, 2013, 1 page, vol. 10—issue 12, https://doi.org/10.1002/ppap.201300083.

Mounir Laroussi, J. Paul Richardson and Fred C. Dobbs, Effects of non-equilibrium atmospheric pressure plasmas on the heterotrophic pathways of bacteria and on their cell morphology, Applied Physics Letters, Jul. 16, 2002, 4 pages, vol. 81, No. 4, https://doi.org/10.1063/1.1494863.

Mark Peplow, Plasma Power, article in Scientific American 321, 6, Dec. 14-15, 2019, doi:10.1038/scientificamerican1219-14.

Laroussi et al., Plasma interaction with microbes, New Journal of Physics, Jan. 2003, 11 pages, vol. 5, IOP Publishing, https://iopscience.iop.org/article/10.1088/1367-2630/5/1/341.

Hiromasa Tanaka et al., Plasma-Treated Solutions (PTW) in Cancer Therapy, Cancers, Apr. 6, 2021, 19 pages, MDPI, https://doi.org/10.3390/cancers13071737.

Andrei V. Pipa and Ronny Brandenburg, The Equivalent Circuit Approach for the Electrical Diagnostics of Dielectric Barrier Discharges: The Classical Theory and Recent Developments, Atoms, Jan. 23, 2019, 18 pages, vol. 7, issue 7, MDPI, doi:10.3390/atoms7010014.

\* cited by examiner

Condition of the wound on the 1st day:
On the 1st day, it is obvious that the vascular stent is not covered by the new tissue.

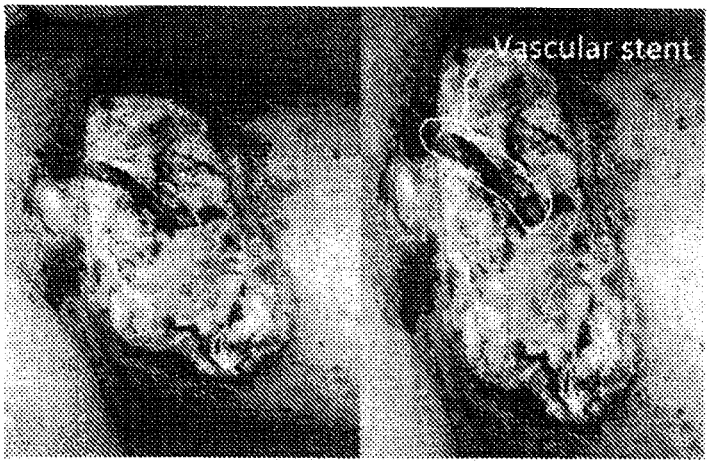

The enclosed place is the vascular stent.

Wound condition on the 2nd day:

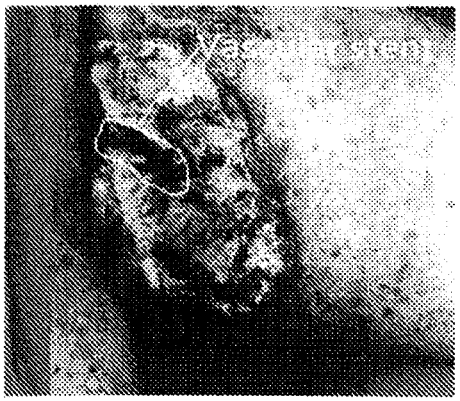

On the 2nd day, new granulation tissue can be seen.

Wound condition after 3-4 days:

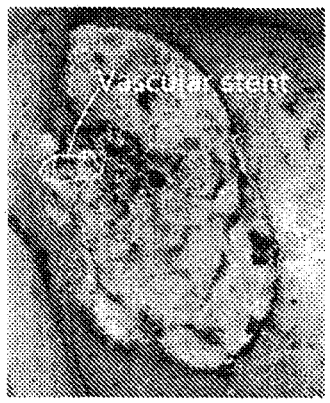

On the 3rd - 4th day, the stent is largely covered by the new tissue.

Wound condition after 7 days:

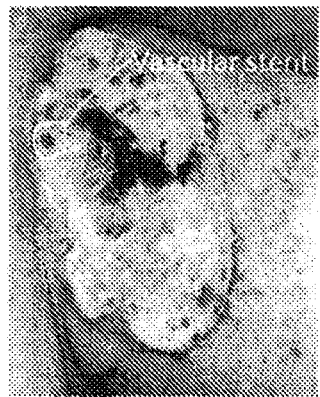

On the 7th day, only a tiny area of the stent is still not covered.

*FIG. 6*

CAPACITOR CAPABLE OF RELEASING REACTIVE OXYGEN SPECIES AND REACTIVE NITROGEN SPECIES AFTER POWERING

BACKGROUND OF INVENTION

Field of the Invention

The present invention relates to a capacitor, and more particularly to a capacitor perforated to form honeycomb shape and powered, the air surrounding the capacitor flowing through the capacitor is ionized to the oxygen species and nitrogen species via heating and charge-discharge, generates plasma at room temperature and atmospheric pressure and releases the reactive oxygen species and reactive nitrogen species healing and helpful for body healing.

Description of Related Art

Over the recent years, much research has indicated that at the time of the plasma becoming, the reactions of ultraviolet rays, neutral particles, active particles, electrons and ions are generated. These high-energy particles can convert oxygen in the atmosphere into reactive oxygen species (ROS). ROS is very important for cells and living bodies, that is, it is an ion byproduct generated during the process while living body proceeds with aerobic metabolism. The generation of ROS is suspected to be direct to the damage of cell structures, which is called oxidative stress. The said reactants will disturb the metabolism process of the biologic tissues and block cell divisions, thereby achieving the treatment effects. Further, the research as found that cancer cells are more easily to be influenced by these effects than healthy cells.

Much research is related to the plasma applied in the medical field, for example sterilization and cancer therapy. Back in 2002, Richardson's team studied the issues related to plasma applied in sterilization, wound healing and cancer and tumor therapy, and the results shown that the curative effect of plasma was highly related to the species of bacteria. In 2003, Laroussi et al. adopted a system, namely Resistive Barrier Discharge (RBD), to generate atmospheric-pressure plasma and proceeded with further research, and the found that the difference of sterilization effect of plasma was due to the different tensile strengths induced by the surface of cell wall of different cell species for responding to the plasma electric field. However, the surface of each kind of bacteria comprises probably few or many protuberances, the prospect of the plasma applied in sterilization is optimistic if the operation condition is appropriate enough to achieve the effect of fracture of the bacteria plasma static electricity. As for its application in cancer therapy, recently some research (e.g., researches by The George Washington University and Nagoya University) indicated that low-temperature plasma has the capacity of killing or preventing target cancer cells and causing less impact on the adjacent normal cells. It was even found that plasma can enhance absorption of medical molecules by the cells. This ideal feature makes plasma a good candidate adjuvant for compound chemical therapies. Moreover, such features like portability, adjustable composition, minimal hurt to the human body, and gaseous state for easy access to narrow holes are making plasma a potential aid for cancer treatment.

Based on the foregoing researching results, the plasma provides sterilization and curing effect, and the inventor proposed the present invention after extensive research and practical improvements.

SUMMARY OF THE INVENTION

The primary objective of the present invention is to provide a capacitor capable of releasing reactive oxygen species and reactive nitrogen species after powering.

The primary feature of the invention is that, after the capacitor is perforated to form honeycomb shape and powered, the air surrounding the capacitor flowing through the capacitor is ionized to the oxygen ion and nitrogen ion via heating and charge-discharge, generates plasma at room temperature and atmospheric pressure and releases the reactive oxygen ions and reactive nitrogen ions healing and helpful for body healing.

BRIEF DESCRIPTION OF THE DRAWINGS

FIG. 6 is an illustrative view of an example of the application of the invention in wound healing.

DETAILED DESCRIPTION OF EMBODIMENTS OF THE INVENTION

Figure 1:
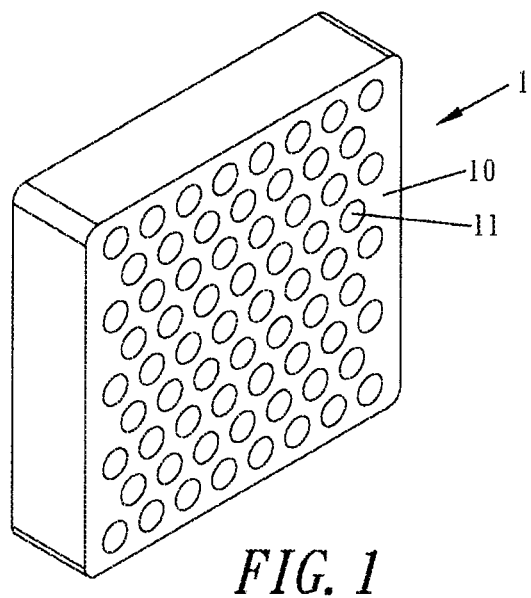
FIG. 1 is a perspective view of a single capacitor according to one embodiment of the invention.
Figure 2:
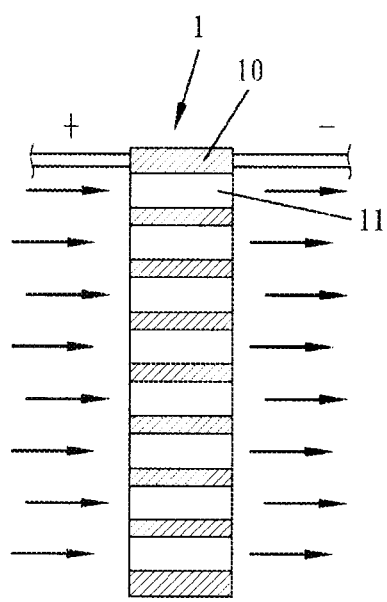
FIG. 2 is a sectional view of a single capacitor according to one embodiment of the invention.
Figure 3:
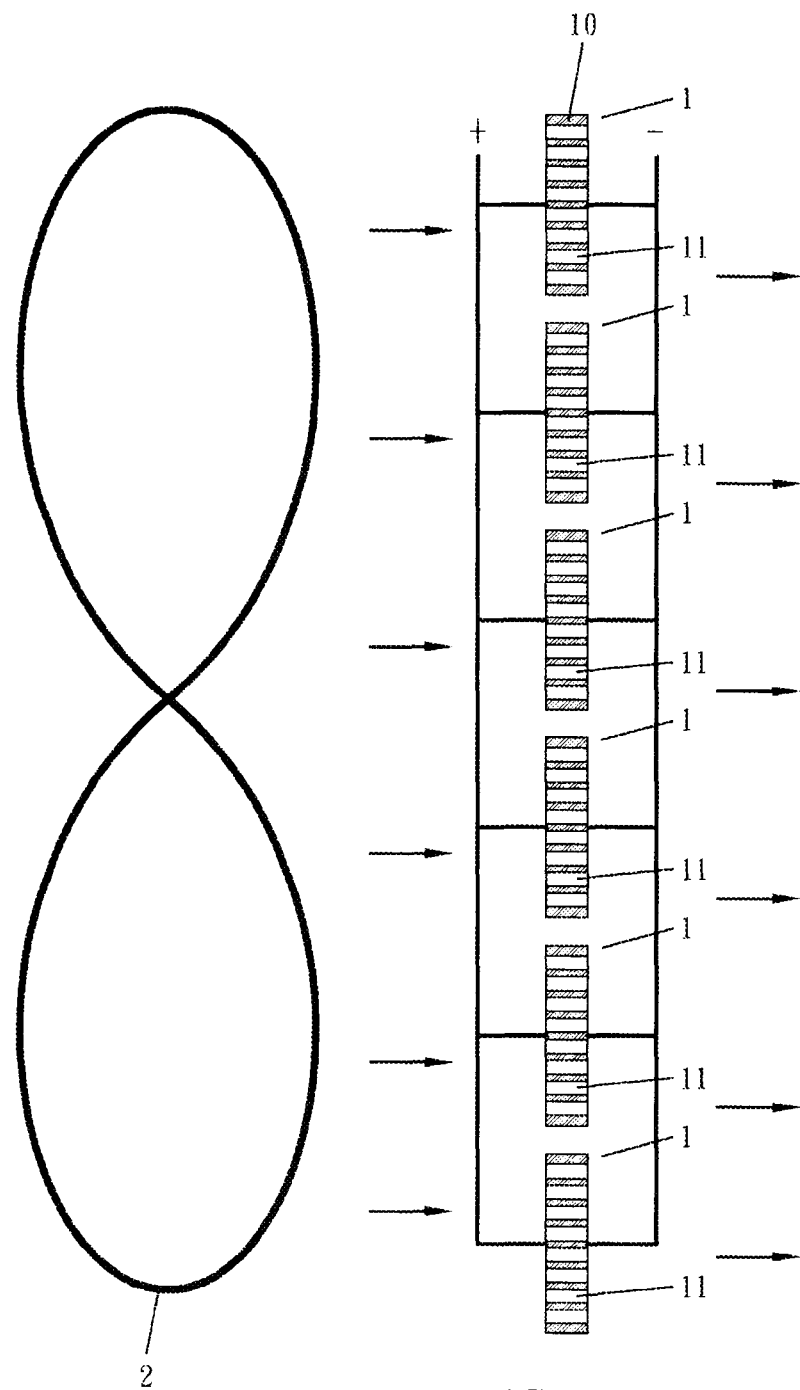
FIG. 3 is a lateral view of the embodiment of the invention made up of multiple capacitors connected in series or in parallel.

As shown in FIGS. 1 and 2, a capacitor 1 is composed of a dielectric material 10, comprising a highly dielectric material, such as BaTio3, $HfO_2$, lead zirconate titanate (PbZrxTi1-xO3), PZT, strontium bismuth tantalate ($SrBi_2Ta_2O_9$ or SBT), AlN and the derivative material thereof or other highly dielectric material. The capacitor 1 is designed with a plurality of through holes 11, the diameter of each hole 11 can be 0.5~1.5 mm so that the holes 11 can be used as the air gap to supply plasma gas, and a fan 2 (as shown in FIG. 3) is provided to blow air to the capacitor 1 to increase the gas flow. A voltage is connected to the two corresponding electrode edges of the capacitor 1 (can be municipal electricity of 110 v/60 Hz or alternating electricity of higher voltages and frequencies).

When applying a voltage to the two electrode edges of the capacitor 1, the dielectric material 10 of the capacitor 1 will heat and warm up and remain at a designed temperature (e.g., 200° C. or so). The capacitor 1 will effectively reduce the ionization threshold of the air molecules due to the heating effect of heating up. The tiny holes 11 of the capacitor 1 will significantly increase the strength of the gap electric field via the process of charging and recharging of the capacitor 1 so that the air being warmed by the capacitor 1 is ionized to oxygen ions and nitrogen ions, thereby releasing the atmospheric room temperature pressure plasma of the reactive oxygen species (ROS) and reactive nitrogen species (RNS) helpful to human body, and further the fan blows to continuously supply gas so that the plasma can be generated continuously. Moreover, the capacitor 1 comprises a plurality of honeycomb tiny holes 11 connect in series to the plasma current, accumulating the minimal plasma current to a high plasma strength, thus increasing the density of the output plasma.

In production, as shown in FIG. 3, multiple capacitors 1 are connected in series or in parallel to form a device, to increase the output amount of reactive oxygen species (ROS) and reactive nitrogen species (RNS) to be used.

Figure 4:
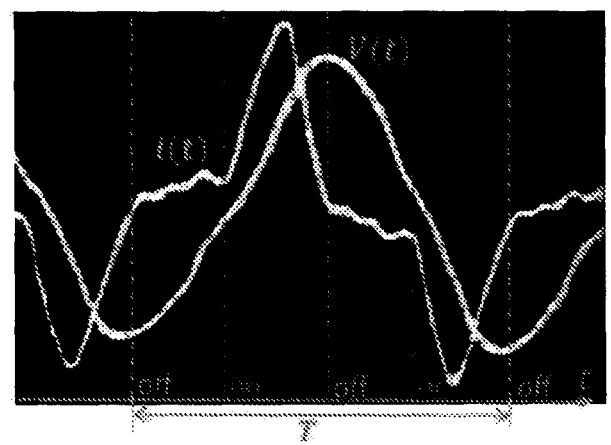
FIG. 4 is a diagram of the electrical characteristics—i(t), V(t) and t—of the reactor of one embodiment of the invention shown on the oscillometer during actual operation.

The process of generating plasma by the system of the present invention can be understood by observing the changes of the applied voltage V(t), the current i(t) and the quantity of electric charge Q(V) (The following description is in reference to the theoretical statements from A. V. Pipa and R. Brandenburg, Atoms 7010014, and Atoms 2019, 7, 14). FIG. 4 shows the electrical characteristics—i(t), V(t) and t—of the reactor of the invention on the oscillator during an actual operation. As can be seen, when the applied sine voltage V(t) increases gradually from the off point on the left end, the waveform of the current i(t) increases gradually. However, when V(t) rises to the on point, i(t) rises rapidly to a peak value. This means the discharging is on, and plasma is generated. However, when the voltage value continues to rise, i(t) descends from the peak value. When V(t) reaches maximum Vmax, i(t) changes to the minimum instead. The off point in FIG. 4 indicates disappearance of the discharging effect, and extinguishing of plasma. When V(t) descends gradually again and changes toward the other polarity, the waveform of the current i(t) repeats the previous change, only with changed polarity. When reaching the on point, the current—i(t) rises to the peak in the opposite direction, and plasma is on again. However, when the voltage rises again to—Vmax point, plasma is off again, and now i(t) is reduced again. This happens repeatedly, and the above reaction occurs in cycles. Accordingly, the reactor is repeatedly charged and discharged, and plasma is off and on in cycles.

Figure 5:
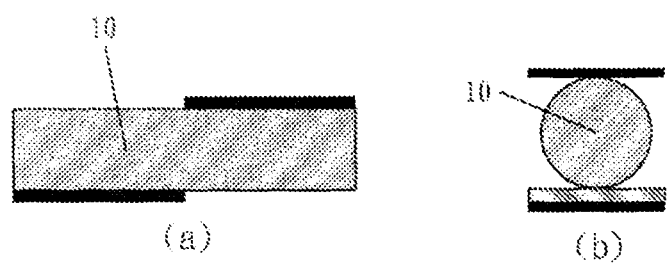
FIG. 5 is geometric structural view of symmetric and asymmetric electrodes according to embodiments of the invention.

The above electrodes can be configured like (a) or (b) in FIG. 5, which are respectively symmetric and asymmetric geometric structures. Different positions of the electrodes will cause different distribution of the electric field, and will consequently affect the generation of plasma. When an uneven electric field is applied on an uneven dielectric material 10, stray inductance will be generated in the dielectric material 10, leading to unstable and unevenly distributed plasma. The example of electrode placement shown in FIG. 5 will affect the quantity of electric charge induced by the dielectric material 10.

An example of application of the present invention is wound healing as shown in FIG. 6. The patient suffering from cancer must undergo a surgery to place a stent in the blood vessel. After the surgery, the present invention is used for wound healing. As shown in FIG. 6, it can be seen that the present invention can help the wound to be healed rapidly, so that the cells can obtain sufficient energy and nutrition for tissue regeneration.

It can be concluded from the above descriptions that, when the capacitor is punched with through holes into a honeycomb form and is electrified, the holes can be used as the air gaps to supply plasma gas, and the air around the capacitor will flow through the capacitor and be heated to generate plasma under room temperature and atmospheric pressure during charging and discharging by the capacitor, and consequently, reactive oxygen species and reactive nitrogen species are released to help body healing.

What is claimed is:

1. A capacitor capable of releasing reactive oxygen species and reactive nitrogen species after powering, the capacitor having two corresponding electrode edges and composed of a high dielectric material comprising barium titanate (BaTio3), hafnium dioxide ($HfO_2$), lead zirconate titanate (PZT), strontium bismuth tantalate (SBT), aluminum nitride (AlN) or derivatives thereof, wherein a voltage is connected to the two corresponding electrode edges of the capacitor and the capacitor generates a heating temperature, the capacitor is punched with a plurality of through holes used as an air space for supplying air, the air surrounding the capacitor after heating and the charging and recharging function of the capacitor is ionized to oxygen ions and nitrogen ions, thereby generating an atmospheric room temperature pressure plasma and releasing the reactive oxygen species and reactive nitrogen species helpful for the curing of human body.

2. The capacitor capable of releasing reactive oxygen species and reactive nitrogen species after powering of claim 1, wherein a fan is provided to blow to the capacitor for increasing the gas flow.

3. The capacitor capable of releasing reactive oxygen species and reactive nitrogen species after powering of claim 1, wherein the diameter of the hole is less than 1.5 mm.

4. The capacitor capable of releasing reactive oxygen species and reactive nitrogen species after powering of claim 1, wherein the configuration of electrode edges comprises a symmetric or an unsymmetrical geometrical structure.

5. The capacitor capable of releasing reactive oxygen species and reactive nitrogen species after powering of claim 1, wherein the electrode edges can apply an alternating current (AC) voltage with a variety of amplitudes and frequencies.

6. A device capable of releasing reactive oxygen species and reactive nitrogen species after powering, the device comprising at least two capacitors connected together in series or in parallel, each capacitor having two corresponding electrode edges and composed of a high dielectric material comprising barium titanate (BaTio3), hafnium dioxide ($HfO_2$), lead zirconate titanate (PZT), strontium bismuth tantalate (SBT), aluminum nitride (AlN) or derivatives thereof, wherein a voltage is connected to the two corresponding electrode edges of each capacitor and each capacitor generates a heating temperature, each capacitor is punched with a plurality of through holes used as an air space for supplying air, the air surrounding each capacitor after heating and the charging and recharging function of each capacitor is ionized to the oxygen ions and a nitrogen ions, thereby generating an atmospheric room temperature pressure plasma and releasing the reactive oxygen species and reactive nitrogen species helpful for the curing of human body.

* * * * *